United States Patent
Kopperschmidt et al.

(10) Patent No.: US 12,337,093 B2
(45) Date of Patent: *Jun. 24, 2025

(54) METHOD FOR REGULATING THE SUPPLY OF SUBSTITUATE DURING EXTRACORPOREAL BLOOD TREATMENT AND EXTRACORPOREAL BLOOD TREATMENT DEVICE COMPRISING A UNIT FOR REGULATING THE SUPPLY OF SUBSTITUATE

(71) Applicant: FRESENIUS MEDICAL CARE DEUTSCHLAND GMBH, Bad Homburg (DE)

(72) Inventors: Pascal Kopperschmidt, Dittelbrunn (DE); Alfred Gagel, Litzendorf (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 499 days.

This patent is subject to a terminal disclaimer.

(21) Appl. No.: 17/825,294

(22) Filed: May 26, 2022

(65) Prior Publication Data

US 2022/0280707 A1  Sep. 8, 2022

Related U.S. Application Data

(63) Continuation of application No. 13/512,133, filed as application No. PCT/EP2010/006981 on Nov. 16, 2010, now Pat. No. 11,376,353.

(30) Foreign Application Priority Data

Nov. 26, 2009 (DE) ............ 10 2009 055 995.7

(51) Int. Cl.
*B01D 61/32* (2006.01)
*A61M 1/16* (2006.01)
(Continued)

(52) U.S. Cl.
CPC ............ *A61M 1/342* (2013.01); *A61M 1/16* (2013.01); *A61M 1/1601* (2014.02);
(Continued)

(58) Field of Classification Search
CPC .... A61M 1/16; A61M 1/1601; A61M 1/1603; A61M 1/1613; A61M 1/1617;
(Continued)

(56) References Cited

U.S. PATENT DOCUMENTS 5,092,836 A  3/1992 Polaschegg
5,947,689 A  9/1999 Schick
(Continued)

FOREIGN PATENT DOCUMENTS

DE  600 30 460 T2  3/2007
DE  600 37 408 T2  4/2008
(Continued)

OTHER PUBLICATIONS

Pries, A.R., et al. "Microvascular blood viscosity in vivo and the endothelial surface layer," AJP-Heart Circ Physiol, First published Jul. 22, 2005, H2657-H2664, vol. 289.
(Continued)

*Primary Examiner* — Claire A Norris
(74) *Attorney, Agent, or Firm* — Kilyk & Bowersox, P.L.L.C.

(57) ABSTRACT

A method that regulates supply of substituate in an extracorporeal blood treatment with an extracorporeal blood treatment apparatus comprising a dialyzer divided by a semipermeable membrane into a blood chamber and a dialyzing fluid chamber and a device for supplying substituate. An extracorporeal blood treatment apparatus that includes a device for regulating supply of substituate. Regulation of supply of substituate in the extracorporeal blood treatment takes place as a function of the rheological loading
(Continued)

of the dialyzer. To regulate supply of substituate during extracorporeal blood treatment, rheological loading of the dialyzer is determined from transmembrane pressure on the dialyzer and flow resistance of the dialyzer and substituate rate is increased or reduced according to the loading. The selection of dialyzer parameters or blood parameters is therefore no longer necessary and the distinction between pre-dilution and post-dilution is also made obsolete.

15 Claims, 2 Drawing Sheets

(51) Int. Cl.
*A61M 1/34* (2006.01)
*A61M 1/36* (2006.01)
*B01D 61/24* (2006.01)
*B01D 61/28* (2006.01)

(52) U.S. Cl.
CPC ........ *A61M 1/1603* (2014.02); *A61M 1/1613* (2014.02); *A61M 1/1635* (2014.02); *A61M 1/34* (2013.01); *A61M 1/3403* (2014.02); *A61M 1/341* (2014.02); *A61M 1/3413* (2013.01); *A61M 1/3431* (2014.02); *A61M 1/3434* (2014.02); *A61M 1/3437* (2014.02); *A61M 1/3635* (2014.02); *B01D 61/243* (2013.01); *B01D 61/28* (2013.01); *B01D 61/32* (2013.01); *A61M 1/1617* (2014.02); *A61M 1/36* (2013.01); *A61M 2205/3334* (2013.01); *B01D 2311/14* (2013.01); *B01D 2311/16* (2013.01)

(58) Field of Classification Search
CPC .... A61M 1/1635; A61M 1/34; A61M 1/3403; A61M 1/341; A61M 1/3413; A61M 1/342; A61M 1/3431; A61M 1/3434; A61M 1/3437; A61M 1/36; A61M 1/3635; A61M 2205/3334; B01D 2311/14; B01D 2311/16; B01D 61/243; B01D 61/28; B01D 61/32
USPC ........................................................ 210/646
See application file for complete search history.

(56) References Cited

U.S. PATENT DOCUMENTS

| | | | |
|---|---|---|---|
| 6,814,864 B1 | 11/2004 | Favre et al. | |
| 2002/0023880 A1 | 2/2002 | Pedrini et al. | |
| 2002/0174721 A1 | 11/2002 | Gross | |
| 2005/0065459 A1 | 3/2005 | Zhang et al. | |
| 2006/0157408 A1 | 7/2006 | Kuroda et al. | |
| 2006/0254982 A1 | 11/2006 | Kopperschmidt | |
| 2007/0108128 A1 | 5/2007 | Kopperschmidt et al. | |
| 2010/0137777 A1* | 6/2010 | Kopperschmidt .. | A61M 1/3441 604/5.04 |
| 2010/0264086 A1 | 10/2010 | Noack et al. | |
| 2010/0276367 A1 | 11/2010 | Zhang | |
| 2010/0280761 A1* | 11/2010 | Balschat ............... | A61M 1/341 702/19 |
| 2012/0318739 A1 | 12/2012 | Kopperschmidt et al. | |

FOREIGN PATENT DOCUMENTS

| | | |
|---|---|---|
| EP | 1 095 666 | 5/2001 |
| EP | 1 175 917 | 1/2002 |
| EP | 2504044 B1 | 1/2016 |
| JP | 2002126075 A | 5/2002 |
| WO | 0176661 A1 | 10/2001 |
| WO | 03047656 A1 | 6/2003 |
| WO | 2008135193 A1 | 11/2008 |
| WO | 2009056325 A1 | 5/2009 |
| WO | 2009080258 A1 | 7/2009 |
| WO | 2009087092 A1 | 7/2009 |
| WO | 2011063906 A1 | 6/2011 |
| WO | 2013029786 A | 3/2013 |

OTHER PUBLICATIONS

"Hagen-Poiseuille equation" from Wikipedia, pp. 1-10, retrieved from https://en.wikipedia.org/wikilHagen%E2%80%93Poiseuille_equation, printed Oct. 26, 2016.
Chelamcharla et al., Dialyzer membranes as Determinants of the Adequacy of Dialysis, Seminars in Nephrology, Mar. 2005; 25(2):81-89. doi: 10.1016/j.semnephrol.2004.09.014, Elsevier Inc.
Gordge et al., Abnormal Blood Rheology in Progressive Renal Failure: A Factor in Non-immune Glomerular Injury?, Nephrology Dialysis Transplantation, European Dialysis and Transplant Association—European Renal Association, 1988; 3: 257-262.
Notice of Opposition (EPO Form 2300E-PN2301D01) for EP Patent No. EP2504044, published by the European Patent Office, dated Oct. 26, 2016, 5 pages.
Examination Report for Indian Patent Application No. 4550/DELNP/2012, issued by Intellectual Property India, date of dispatch Mar. 5, 2019, including Summary of the Report, 8 pages.
Hearing Notice dated Jun. 3, 2021, for Indian Patent Application No. 4550/DELNP/2012, issued by Intellectual Property India, 3 pages.
International Preliminary Report on Patentability from PCT/EP2010/006981, mailed on Jun. 5, 2012.
PCT International Search Report from PCT/EP2010/006981, mailed on Apr. 26, 2011.

* cited by examiner

METHOD FOR REGULATING THE SUPPLY OF SUBSTITUATE DURING EXTRACORPOREAL BLOOD TREATMENT AND EXTRACORPOREAL BLOOD TREATMENT DEVICE COMPRISING A UNIT FOR REGULATING THE SUPPLY OF SUBSTITUATE

CROSS REFERENCE TO RELATED APPLICATIONS

This application is a continuation application of nonprovisional application Ser. No. 13/512,133, filed Aug. 9, 2012, which is a 371 national phase application of PCT/EP2010/006981, filed Nov. 16, 2010, which claims priority from German Patent Application No. DE 10 2009 055 995.7, filed Nov. 26, 2009.

FIELD OF INVENTION

The present invention relates to a method for regulating the supply of substituate in an extracorporeal blood treatment with an extracorporeal blood treatment apparatus, which comprises a dialyzer divided by a semipermeable membrane into a blood chamber and a dialyzing fluid chamber and a device for supplying substituate. Moreover, the present invention relates to an apparatus for extracorporeal blood treatment with a device for regulating the supply of substituate.

BACKGROUND OF THE INVENTION

Various methods for machine-aided blood cleaning or blood treatment are used in chronic kidney failure in order to remove substances usually eliminated with urine and for fluid withdrawal. In hemodialysis (HD), the patient's blood is conveyed in an extracorporeal blood circuit through the blood chamber of a dialyzer divided by a semipermeable membrane into the blood chamber and a dialyzing fluid chamber, while a dialyzing fluid flows through the dialyzing fluid chamber. A diffuse substance exchange essentially takes place via the membrane of the dialyzer. In the case of hemofiltration (HF), dialyzing fluid does not flow through the dialyzing fluid chamber. Only a convective substance exchange takes place. Hemodiafiltration (HDF) is a combination of the two processes.

The quantity of fluid removed from the patient via the semipermeable membrane of the dialyzer in the case of hemofiltration (HF) or hemodiafiltration (HDF) is fed back to the patient during the blood treatment as substituate, which is either made available ready for use or is obtained from the dialyzing fluid during the blood treatment. The substituate is fed to the extracorporeal blood circuit upstream and/or downstream of the dialyzer. The supply of substituate upstream of the dialyzer is referred to as pre-dilution and downstream of the dialyzer as post-dilution. The substituate rate refers to the quantity of substituate that is supplied in a specific period of time to the blood flowing in the extracorporeal blood circuit.

In order to balance fresh and used dialyzing fluid, which flows into and respectively out of the dialyzing fluid chamber of the dialyzer, use is made of balancing systems in the known blood treatment apparatuses. The balancing of fresh and used dialyzing fluid ensures that no fluid or only a specific quantity of fluid is fed to or removed from the patient.

The ultrafiltration rate at which fluid is removed from the patient is dependent on the transmembrane pressure TMP, which is defined as the pressure difference between the mean blood-side pressure and the mean dialysate-side pressure in the dialyzer. Methods and devices for determining the transmembrane pressure are generally known. EP 0 212 127 A1 and WO 2009/080258 A1, for example, describe a device for determining the transmembrane pressure.

Apart from the transmembrane pressure, the longitudinal flow resistance along the hollow fibers of the semipermeable membrane of the dialyzer on the blood side is of importance for an extracorporeal blood treatment, said longitudinal flow resistance being referred to below as the flow resistance of the dialyzer. It is known that the attenuation of pressure pulses along the hollow fibers of the membrane of the dialyzer is connected with the ratio of the amplitudes of the spectral components of the first and second harmonics to the fundamental component (WO 2008/135193 A1).

The problem underlying the present invention is to provide a method with which the regulation of the substituate rate is enabled during the extracorporeal blood treatment. Moreover, a problem of the present invention is to create an apparatus for extracorporeal blood treatment with an improved regulation of the substituate rate.

SUMMARY OF THE INVENTION

According to the present invention, the solution to these problems takes place with the claimed method for regulating the supply of substituate in an extracorporeal blood treatment with an extracorporeal blood treatment apparatus, as well as the claimed extracorporeal blood treatment apparatus. Advantageous embodiments of the present invention are the subject-matter of dependent claims.

The method according to the present invention and the device according to the present invention are based on the fact that the regulation of the supply of substituate in the extracorporeal blood treatment takes place as a function of the rheological loading of the dialyzer. Account has to be taken of the fact that the substituate rate is not an independent variable which can be regulated solely as a function of the rheological loading of the dialyzer, since the substituate rate is connected with the ultrafiltration rate. The method according to the present invention and the device according to the present invention therefore focus on proceeding from a preset substituate rate at which substituate is fed to the patient taking account of a specific ultrafiltration rate, the preset substituate rate being increased or reduced as a function of the rheological loading of the dialyzer.

The rheological loading of the dialyzer is determined in order to regulate the supply of substituate during the extracorporeal blood treatment and to increase or reduce the substituate rate corresponding to the loading. The selection of dialyzer parameters or blood parameters is no longer necessary. Even the distinction between pre-dilution or post-dilution is obsolete.

The rheological loading of the dialyzer is preferably determined on the basis of the transmembrane pressure or a variable correlating with the transmembrane pressure and the flow resistance or a variable correlating with the flow resistance, wherein the transmembrane pressure or the variable correlating with the transmembrane pressure and the flow resistance or the variable correlating with the flow resistance are ascertained during the extracorporeal blood treatment. It is unimportant here how the transmembrane pressure and the flow resistance are measured. The only decisive factor is that the transmembrane pressure and the flow resistance or variables derived from the transmembrane pressure and the flow resistance are available for the further evaluation, in order to be able to regulate the supply of substituate as a function of transmembrane pressure and flow resistance.

A preferred embodiment of the present invention makes provision to ascertain a first evaluation quantity for the purpose of evaluating the transmembrane pressure or the variable correlating with the transmembrane pressure and a second evaluation quantity for the purpose of evaluating the flow resistance or the variable correlating with the flow resistance. Both ascertained evaluation quantities then form an evaluation pair, which is characteristic of the rheological loading of the dialyzer. The transmembrane pressure and the flow resistance are preferably evaluated within an evaluation scale of 0-100%. The rheology in the dialyzer is completely described by the evaluation pair.

In a preferred embodiment, the evaluation of the dialyzer within the evaluation scale is an input parameter of a 2-dimensional matrix, which assigns to each evaluation pair (priority pair) a value which corresponds to the required change in the substituate rate.

Assigned to each evaluation pair of a large number of evaluation pairs characterising the rheological loading of the dialyzer is a specific value for the amount by which the substituate rate is to be increased or reduced from a preset volume. This assignment of the evaluation pair and the amount of the change in the substituate rate can be stored in a memory. The value by which the preset substituate rate is changed is therefore available in each case for the various evaluation pairs.

A particularly preferred embodiment of the present invention makes provision such that, in order to determine the flow resistance or the variable correlating with the flow resistance, pressure pulses are generated in the extracorporeal blood circuit upstream of the dialyzer and measured downstream of the dialyzer, and that the pressure signal measured downstream of the dialyzer is split up spectrally into a fundamental component and at least one harmonic. The flow resistance or the variable correlating with the flow resistance is then determined on the basis of the ratio of the fundamental component and the at least one harmonic. The measured pressure signal is preferably split up into one fundamental component and two harmonics.

This method has the advantage that the pressure in the extracorporeal blood circuit only needs to be measured downstream of the dialyzer. As pressure pulses, it is possible to measure the pressure pulses which are generated by the blood pump disposed in the extracorporeal blood circuit upstream of the dialyzer, said blood pump generally being an occluding hose pump.

The method according to the present invention and the device according to the present invention can make use of the sensor system which is generally present in any case in the extracorporeal blood treatment apparatus. The evaluation of the data can take place in the central control and computing unit, which is in any case present in the extracorporeal blood treatment apparatus. The device according to the present invention and the method according to the present invention can thus be implemented without major design expenditure.

BRIEF DESCRIPTION OF THE DRAWINGS

An example of embodiment of the present invention will be described in greater detail below by reference to the drawings.

In the figures.

DETAILED DESCRIPTION OF THE INVENTION

Figure 1:
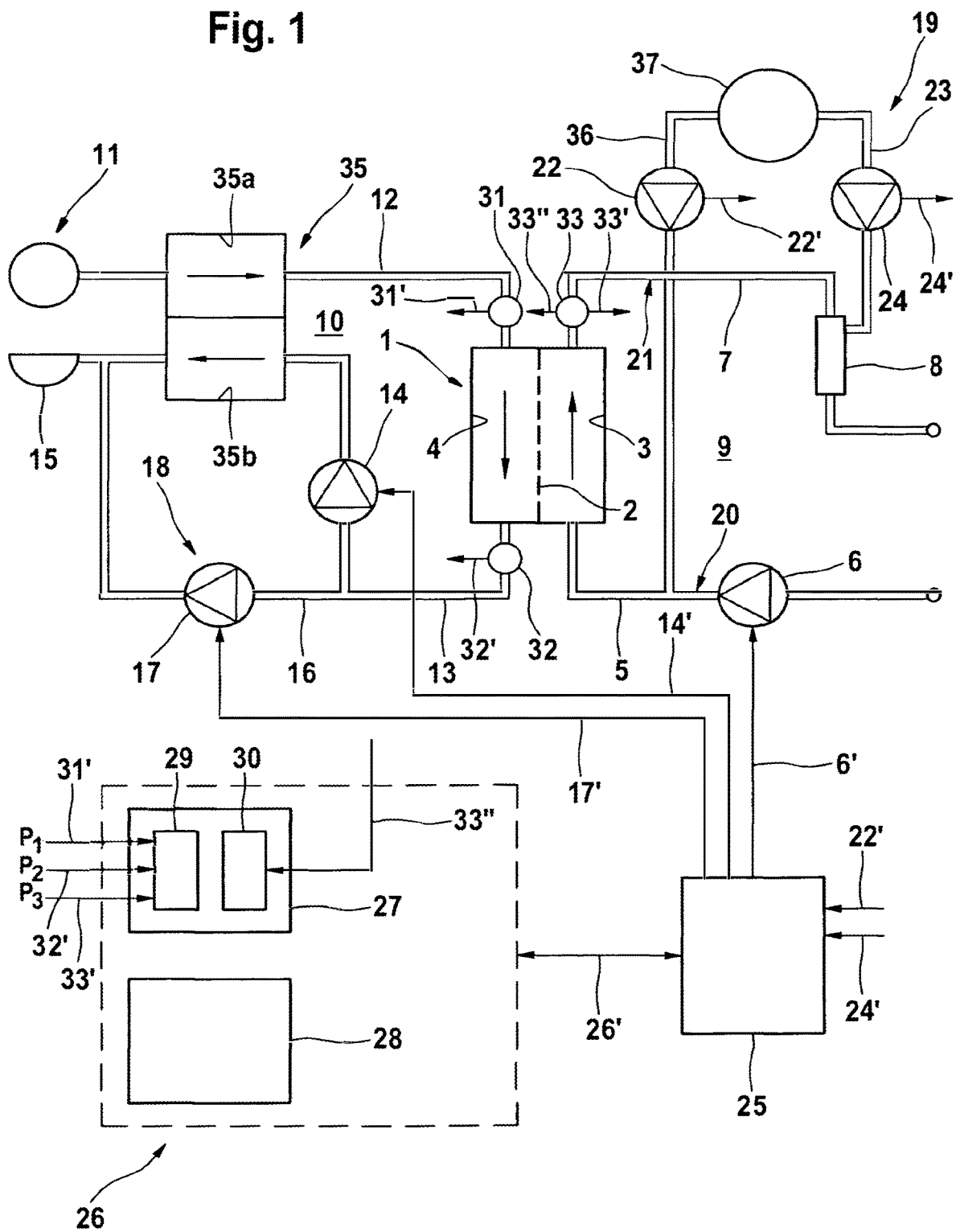
FIG. 1 shows the main components of an extracorporeal blood treatment apparatus according to the present invention in a simplified schematic representation and FIG. 2 shows a matrix, which assigns a value corresponding to the required change in the substituate rate to each evaluation pair characteristic of the rheological loading of the dialyzer.

FIG. 1 shows the main components of the blood treatment apparatus according to the present invention, which is a hemo(dia)filtration apparatus, which comprises a dialyzer (filter) 1 which is divided by a semipermeable membrane 2 into a blood chamber 3 and a dialyzing fluid chamber 4. The inlet of blood chamber 3 is connected to one end of a blood supply line 5, into which a blood pump 6, in particular a roller pump generating pressure pulses, is incorporated, while the outlet of the blood chamber is connected to one end of a blood discharge line 7, into which a drip chamber 8 is incorporated. Blood supply line and blood discharge line 5, 7 form, with blood chamber 3 of the dialyzer, extracorporeal blood circuit 9 of the hemodiafiltration apparatus. Blood supply line and blood discharge line 5, 7 are hose lines of a hose set (disposable) inserted into the hemodiafiltration apparatus.

Dialyzing fluid system 10 of the hemodiafiltration apparatus comprises a device 11 for making available dialyzing fluid, which is connected via the first section of dialyzing fluid supply line 12 to the inlet of first balancing chamber half 35a of a balancing device 35. The second section of dialyzing fluid supply line 12 connects the outlet of first balancing chamber half 35a to the inlet of dialyzing fluid chamber 4. The outlet of dialyzing fluid chamber 4 is connected via the first section of a dialyzing fluid discharge line 13 to the inlet of second balancing chamber half 35b. A dialyzing fluid pump 14 is incorporated into the first section of dialyzing fluid discharge line 13. The outlet of second balancing chamber half 35b is connected via the second section of dialyzing fluid discharge line 13 to a drain 15. An ultrafiltrate line 16, which also leads to drain 15, branches off from dialyzing fluid discharge line 13 upstream of dialyzing fluid pump 14. An ultrafiltration pump 17 is incorporated into ultrafiltrate line 16. In commercially available apparatuses, balancing device 35 comprises two parallel balancing chambers which are operated anti-cyclically. For reasons of simplification, only one balancing chamber is represented here.

During the dialysis treatment, the patient's blood flows through blood chamber 3 and the dialyzing fluid flows through dialyzing fluid chamber 4 of the dialyzer. Balancing device 35 ensures that only as much dialyzing fluid can be supplied via the dialyzing fluid supply line as dialyzing fluid can be discharged via the dialyzing fluid discharge line. A preset quantity of fluid (ultrafiltrate) can be withdrawn from the patient at a preset ultrafiltration rate with ultrafiltration pump 17. Ultrafiltration pump 17 is thus part of a device for removing fluid from the blood flowing in extracorporeal circuit 9 through membrane 2 of dialyzer 1, which is referred to as ultrafiltration device 18.

In order to feed the fluid back to the patient, the hemodiafiltration apparatus comprises a substitution device 19, with which a substitution fluid (substituate) can be fed to the blood that is flowing through arterial branch 20 (pre-dilution) and/or venous branch 21 (post-dilution) of extracorporeal blood circuit 9. Substitution device 19 comprises a device 37 for making available substituate, from which a first substituate line 36, into which a first substituate pump 22 is incorporated, leads to the section of blood supply line 5 between blood pump 6 and blood chamber 3. A second substituate line 23, into which a second substituate pump 24 is incorporated, leads from device 37 for making available substituate to drip chamber 8. If the hemodiafiltration apparatus is to be operated solely with post-dilution or pre-dilution, the one or other substituate pump together with the respective substituate line can be dispensed with.

Moreover, the hemodiafiltration apparatus comprises a central control and computing unit 25, which is connected via control lines 6', 14', 17', 22', 24' to blood pump 6, dialyzing fluid pump 14, ultrafiltration pump 17 and first and second substituate pump 22, 24.

The extracorporeal blood treatment apparatus comprises a device 26 for regulating the supply of the substituate, which is represented in dashed lines in FIG. 1. Device 26 for regulating the supply of substituate is represented in FIG. 1 as a separate device. It can however also be a component of central control and computing unit 25. Device 26 for regulating the supply of substituate is connected to central control and computing unit 25 via a data line 26', so that the regulating device can exchange data with the control unit, and in particular can correspondingly control substituate pumps 22, 24 in order to adjust substituate rate Q.

Device 26 for regulating the supply of substituate comprises means 27 for determining the rheological loading of the dialyzer and means 28 for regulating the substituate rate.

Means 27 for determining the rheological loading of the dialyzer in turn comprises means 29 for determining the transmembrane pressure on the dialyzer or a variable correlating with the transmembrane pressure and means 30 for determining the flow resistance of the dialyzer or a variable correlating with the flow resistance. The flow resistance of the dialyzer is to be understood as the longitudinal flow resistance along the hollow fibers of semipermeable membrane 2 of dialyzer 1 on the blood side.

Means 29 for determining the transmembrane pressure (TMP) can be designed in different ways. The measuring device described in EP 0 212 127 A1, for example, can be used to determine the transmembrane pressure. In the present example of embodiment, means 29 for determining the transmembrane pressure comprise a first pressure sensor 31 disposed in dialyzing fluid supply line 12 upstream of dialyzing fluid chamber 4 of dialyzer 1, a second pressure sensor 32 disposed in dialyzing fluid discharge line 16 downstream of the dialyzing fluid chamber of the dialyzer and a third pressure sensor 33 disposed in blood return line 21 downstream of chamber 3 of dialyzer 1. Pressure sensors 31, 32, 33 are connected via data lines 31', 32', 33' to means 29 for determining the transmembrane pressure. Pressure $P_1$ upstream and pressure $P_2$ downstream of the dialyzing fluid chamber are measured in dialyzing fluid system 10 by pressure sensors 31 and 32 and pressure $P_3$ downstream of the blood chamber is measured in extracorporeal blood circuit 9 by pressure sensor 33.

Means 29 for determining transmembrane pressure TMP comprise a suitable computing unit, which calculates the transmembrane pressure according to the following equation:

$$TMP = P_3 - \frac{P_1 + P_2}{2}$$

The ascertained value for transmembrane pressure TMP is evaluated as follows. In order to evaluate transmembrane pressure TMP, a first evaluation quantity HEMO Priority is calculated according to the following equation from the measured value for transmembrane pressure TMP and a preset lower limiting value for the transmembrane pressure $TMP_{LIMIT\_LOWER}$ and a preset upper limiting value for the transmembrane pressure $TMP_{LIMIT\_UPPER}$ as well as a preset value range for the transmembrane pressure $TMP_{LIMIT\_RANGE}$. Parameters $TMP_{LIMIT\_LOWER}$, $TMP_{LIMIT\_UPPER}$ and $TMP_{LIMIT\_RANGE}$ are ascertained empirically.

$$HEMO\_Priority = ((TMP - TMP_{LIMIT\_LOWER})/TMP_{LIMIT\_RANGE}) \times 100\%$$

wherein $TMP_{LIMIT\_RANGE} = TMP_{LIMIT\_UPPER} - TMP_{LIMIT\_LOWER}$

Apart from transmembrane pressure TMP, the flow resistance of the dialyzer is ascertained in order to determine the rheological loading of dialyzer 1.

Means 30 for determining the flow resistance comprise means for measuring pressure pulses, which are propagated in the longitudinal direction over the hollow fibers of the semipermeable membrane of the dialyzer on the blood side. The pressure pulses are generated by blood pump 6, which is an occluding hose pump, in particular a roller pump. In the present example of embodiment, pressure sensor 33 disposed downstream of blood chamber 3 in blood return line 21 is used to measure the pressure pulses generated by blood pump 6. A second data line 33'' therefore leads from pressure sensor 33 to means 30 for determining the flow resistance. In order to determine the flow resistance, the pressure signal measured by pressure sensor 33 is split up spectrally into a fundamental component $G_0$ and first and second harmonics $H_1$ and $H_2$, since the attenuation of the pressure pulses along the hollow fibers is connected with the ratio of the amplitudes of the spectral components of first and second harmonics $H_1$ and $H_2$ to fundamental component $G_0$. The theoretical relationship is described in WO 2008/135193 A1.

In order to regulate the substituate flow, the flow resistance is also evaluated as follows. A second evaluation quantity BLKD_priority is calculated from fundamental component $G_0$ and first and second harmonics $H_1$ and $H_2$ as well as empirically established parameters $K_{1,2}$, $M_{1,2}$ and $\alpha$ according to the following equation:

$$BLKD\_Priority = \alpha \times \left( \frac{G_0/H_1 - K_1}{2M_1} + \frac{G_0/H_2 - K_2}{2M_2} \right)$$

The first and second evaluation quantities form an evaluation pair (Hemo_Priority/BLKD_Priority), which is characteristic of the rheological loading of the dialyzer.

The frequency of the fundamental component of the pressure pulses results from the control of blood pump 6. The frequencies of the first and second harmonics of the fundamental component are therefore also known. The splitting-up of the continuous pressure signal into its spectral components preferably takes place with a Fourier transform, particularly preferably by digitalising the measured values of pressure sensor 33 with a discrete Fourier transform, which is carried out in a suitable computing unit.

The advantage of the analysis of the pressure pulses for the determination of the flow resistance lies in the fact that only one sensor downstream of the dialyzer is required. A sensor upstream of the dialyzer, on the other hand, is not required. It is however also possible to determine the flow resistance or a variable correlating with the flow resistance using measurements with four pressure sensors upstream and downstream of the dialyzer on the blood side and dialyzing fluid side. It is also possible to determine approximately the flow resistance or a variable correlating with the flow resistance using a measurement with two pressure sensors downstream of the dialyzer on the blood side and dialyzing fluid side, in that the pressures upstream of the dialyzer on the blood side and dialyzing fluid side are estimated on the basis of operational parameters.

Since the rheological loading of the dialyzer is determined both on the basis of the transmembrane pressure and the flow resistance, the measurement of the transmembrane pressure is sufficient with only two or three pressure sensors instead of the known measurement with four pressure sensors, although the two-point and the three-point measurement of the transmembrane pressure have not always proved to be reliable in practice, since an unsteady behaviour in the region of particularly high transmembrane pressures can occur with the two-point and the three-point measurement.

In the present example of embodiment, the transmembrane pressure and the flow resistance are evaluated in such a way that the evaluation quantities are scaled within an evaluation scale of 0 to 100%. The rheological loading of the dialyzer can be completely described as a point in a two-dimensional coordinate system. The regulation of the substituate rate is based on keeping the rheological loading inside a target area of the matrix. The regulation takes place irrespective of whether a post-dilution or pre-dilution is present.

Figure 2:
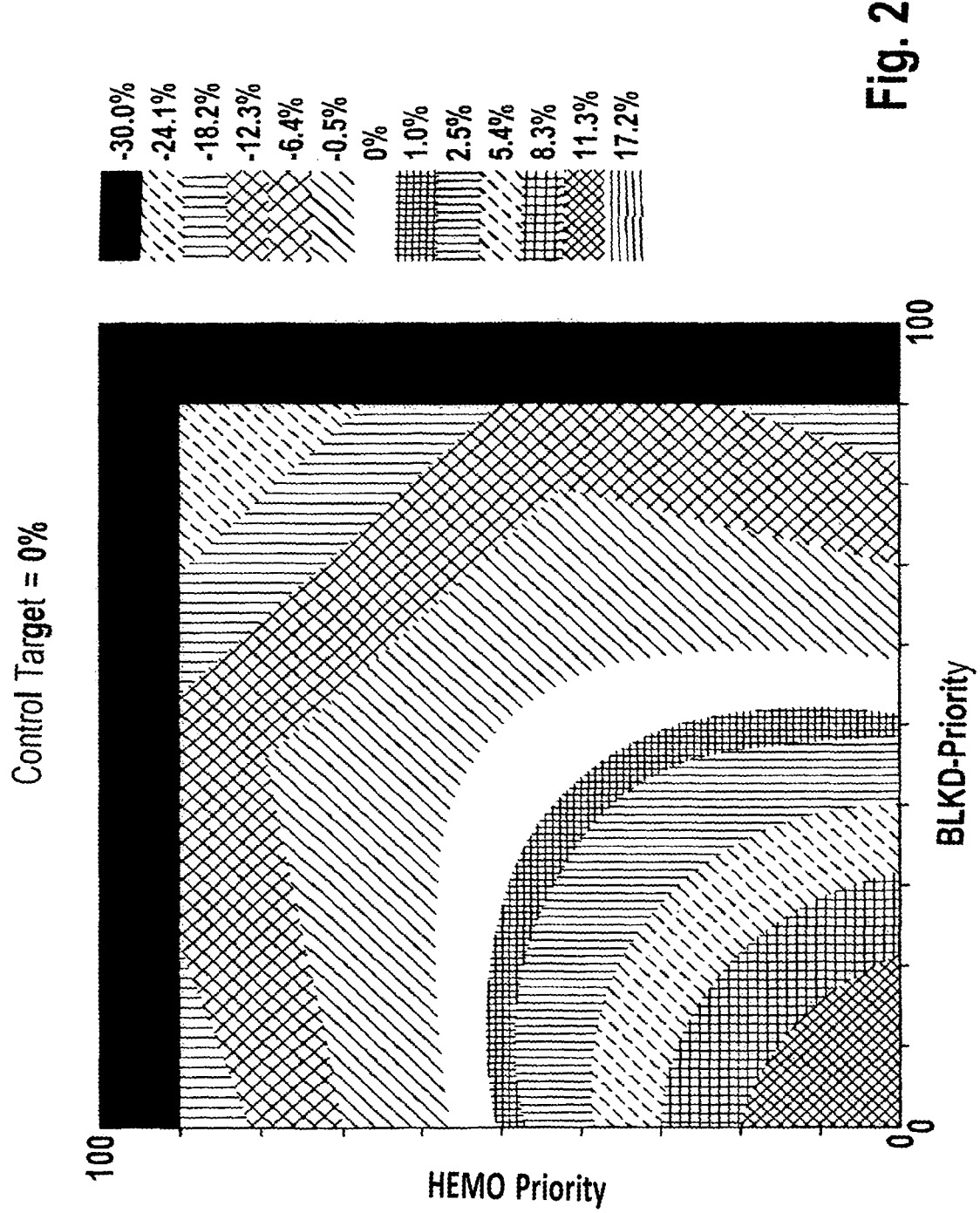

FIG. 2 shows the two-dimensional matrix, which assigns to each evaluation pair (priority pair) a value which corresponds to the required change in the substituate rate. Consequently, a specific value for the amount of the change in the preset substituate rate is assigned to each value pair stored in the matrix. Inside the matrix there is a nominal line (value range) which connects the evaluation pairs to one another which correspond to the desired dialyzer loading. The nominal line is a line which consists mathematically of the connection in a line running linearly to the priorities and a circular line running around the priority pair (0,0). If the priority pair lies on the nominal line, the substituate rate remains unchanged. The nominal line (value range) is marked in FIG. 2 as an unshaded area. The amount of the change in the substituate rate is represented in FIG. 2 by the density of the shading. The scale on the right in FIG. 2 assigns corresponding changes in the substituate rate to the shaded areas in the coordinate system on the left. The control target here is the unshaded area (0%), which is equivalent to an unchanged substituate dose.

Required substituate rate change α is determined from the matrix in device 26 for regulating the supply of substituate. The substituate rate to be newly adjusted $Q_{sub,new}$ is calculated as follows:

$$Q_{sub,new} = Q_{sub,old}(1+\alpha)$$

A specific ultrafiltration rate, which is set using ultrafiltration device 18, is preset for the extracorporeal blood treatment. Furthermore, a selection is made as to whether fluid is to be supplied to or removed from the patient or whether fluid is neither to be supplied to nor removed from the patient. If, for example, fluid is to be removed from the patient, central control and computing unit 25 presets a specific substituate rate. This substituate rate is then rated in such a way that less substituate is supplied to the extracorporeal blood circuit than fluid is removed via membrane 2 of dialyzer 1 by ultrafiltration device 18. This preset substituate rate is increased or reduced by device 26 in order to regulate the supply of substituate according to the method described above. The extracorporeal blood treatment is thus carried out under optimum conditions for the dialyzer.

The regulation of the substituate addition provides not only for a change in the substituate rate, but also a distribution of the supply of substituate upstream and downstream of the dialyzer (pre-dilution and post-dilution). In the case of the supply of substituate both upstream and downstream of the dialyzer, the total dilution quantity for post- and pre-dilution is changed according to the matrix. As a determining parameter for a change instruction for the total dilution quantity, use is made here of the distance of the value pair in the coordinate system characteristic of the rheological loading of the dialyzer from the coordinate origin (0,0) and the angle between the imaginary line, which runs through the coordinate origin (0,0) and the characteristic evaluation pair, and the X-axis or alternatively the Y-axis. Device 26 for regulating the supply of substituate, together with central control and computing unit 25, then sets the flow rates of substituate pumps 22 and 24 in accordance with the ascertained distance and angle.

What is claimed is:

1. An apparatus for hemodiafiltration, comprising:
an extracorporeal blood circuit comprising a blood pump;
a dialyzing fluid system;
a dialyzer divided by a semipermeable membrane into a blood chamber and a dialyzing fluid chamber, the blood chamber being part of the extracorporeal blood circuit, the dialyzing fluid chamber being part of the dialyzing fluid system, and the semipermeable membrane comprises dialyzer fibers;
a sensor system configured for measuring transmembrane pressure (TMP) to determine a measured TMP value, and configured for measuring longitudinal flow resistance along the dialyzer fibers to determine a measured flow resistance value;
a substituate dose rate controller configured to increase or decrease a rate of dosing substituate to the extracorporeal blood circuit; and
a control unit in communication with the sensor system and the substituate dose rate controller, the control unit being configured to (a) determine an adjustment to a rate of dosing substituate into the extracorporeal blood circuit, based on both the measured TMP value and the measured flow resistance value, and (b) adjust the rate of dosing substituate into the extracorporeal blood circuit based on the determined adjustment.

2. The apparatus for hemodiafiltration of claim 1, wherein the blood pump is arranged along the extracorporeal blood circuit upstream of the blood chamber.

3. The apparatus for hemodiafiltration of claim 1, wherein the sensor system comprises a three-point measuring system.

4. The apparatus for hemodiafiltration of claim 1, wherein the sensor system comprises a pressure pulse measuring sensor for measuring the longitudinal flow resistance along the dialyzer fibers.

5. The apparatus for hemodiafiltration of claim 1, wherein the sensor system comprises a blood pressure sensor in sensing communication with the extracorporeal blood circuit downstream of the blood chamber, the blood pressure sensor being connected to at least two data lines.

6. The apparatus for hemodiafiltration of claim 5, wherein the control unit comprises a control and computing unit in communication, through data lines including the at least two data lines, with the sensor system, the blood pump, and the substitute dose rate controller.

7. The apparatus for hemodiafiltration of claim 1, wherein the control unit is configured to: scale the determined measured TMP value to form a first scaled value within an evaluation scale of from 0 to 100%; scale the determined measured flow resistance value to form a second scaled value within an evaluation scale of from 0 to 100%; form a priority pair that comprises the a first scaled value and the second scaled value; and plot the priority pair on a two-dimensional matrix that comprises a two-dimensional coordinate system, such that the priority pair comprises a point in the two-dimensional coordinate system.

8. The apparatus for hemodiafiltration of claim 1, wherein the control unit is configured to (1) plot a first evaluation quantity (HEMO_Priority) based on the determined measured TMP value, (2) plot a second evaluation quantity (BLKD_Priority) based on the determined measured flow resistance value, (3) form a priority pair (HEMO_Priority/BLKD_Priority) from the first evaluation quantity and the second evaluation quantity, (4) compare the priority pair to priority pairs stored in a memory that assigns to each priority pair a substitute dose rate increase or decrease value, (5) based on the comparison, assign a corresponding determined adjustment value for adjusting a rate of dosing substitute into the extracorporeal blood circuit, and (6) control a rate of dosing substitute into the extracorporeal blood circuit, based on the priority pair and the corresponding determined adjustment value.

9. The apparatus for hemodiafiltration of claim 8, wherein the priority pairs stored in the memory comprise priority pairs in a two-dimensional matrix that assigns to each priority pair a substitute dose rate adjustment, increase or decrease value.

10. The apparatus for hemodiafiltration of claim 1, wherein the substitute dose rate controller comprises a substitute supply device comprising a first substitute pump that is configured to supply substitute at a preset substitute rate to the extracorporeal blood circuit.

11. The apparatus for hemodiafiltration of claim 1, wherein the sensor system comprises:
a first pressure sensor in communication with the dialyzing fluid system upstream of the dialyzing fluid chamber and located along a dialyzing fluid supply line, the first pressure sensor being configured to sense a first pressure and to generate a first pressure signal; and
a second pressure sensor in communication with the dialyzing fluid system downstream of the dialyzing fluid chamber and located along a dialyzing fluid discharge line, the second pressure sensor being configured to sense a second pressure and to generate a second pressure signal, wherein
the sensor system comprises at least two data lines,
the at least two data lines comprise a first blood pressure data line and a second blood pressure data line,
the control unit is configured to receive the first and second pressure signals via respective data lines including the first and second blood pressure data lines,
the blood pump is configured to generate pressure pulses in the extracorporeal blood circuit upstream of the dialyzer,
the semipermeable membrane is configured to transmit and attenuate the pressure pulses,
the control unit is configured to split up a pressure signal measured downstream of the dialyzer into a fundamental component and at least one harmonic,
the longitudinal flow resistance is determined based on a ratio of the fundamental component and the at least one harmonic, and
the sensor system, together with the control unit, is configured to determine the transmembrane pressure via the blood pressure signal, the first pressure signal, and a second pressure signal.

12. A method for controlling a rate of dosing substitute into an extracorporeal blood circuit during a hemodiafiltration treatment with an apparatus, the apparatus comprising the extracorporeal blood circuit, a blood pump, a dialyzing fluid system, a dialyzer divided by a semipermeable membrane into a blood chamber and a dialyzing fluid chamber, a sensor system, a substitute dose rate controller, and a control unit, wherein
the semipermeable membrane comprises dialyzer fibers,
the blood chamber is part of the extracorporeal blood circuit,
the dialyzing fluid chamber being is of the dialyzing fluid system,
the sensor system is configured for measuring transmembrane pressure (TMP) to determine a measured TMP value, and configured for measuring longitudinal flow resistance along the dialyzer fibers to determine a measured flow resistance value,
the substitute dose rate controller is configured to increase or decrease a rate of dosing substitute to the extracorporeal blood circuit,
the control unit is in communication with the sensor system and the substitute dose rate controller,
and the method comprises:
measuring transmembrane pressure (TMP);
determining a measured TMP value;
measuring longitudinal flow resistance along the dialyzer fibers;
determining a measured flow resistance value;
determining, with the control unit, an adjustment to a rate of dosing substitute into the extracorporeal blood circuit, based on both the determined measured TMP value and the determined measured flow resistance value; and
adjusting the rate of dosing substitute into the extracorporeal blood circuit based on the determined adjustment.

13. The method of claim 12, further comprising:
scaling the determined measured TMP value to be within an evaluation scale of from 0 to 100%;
scaling the determined measured flow resistance value to be within an evaluation scale of from 0 to 100%; and
pairing the scaled determined measured TMP value with the scaled determined measured flow resistance value, to form a priority pair, wherein
the determining an adjustment to the rate of dosing substitute into the extracorporeal blood circuit comprises comparing the priority pair to predetermined pairs, each of which is assigned a respective adjustment value.

14. The method of claim 13, wherein
the comparing the priority pair to predetermined pairs comprises comparing the priority pair to predetermined pairs stored in a two-dimensional matrix comprising a two-dimensional coordinate system, and
the priority pair comprises a point in the two-dimensional coordinate system.

15. The method of claim 12, wherein the sensor system comprises a first pressure sensor in communication with the dialyzing fluid system upstream of the dialyzing fluid chamber and located along a dialyzing fluid supply line, the first pressure sensor being configured to sense a first pressure and to generate a first pressure signal, a second pressure sensor in communication with the dialyzing fluid system downstream of the dialyzing fluid chamber and located along a dialyzing fluid discharge line, the second pressure sensor being configured to sense a second pressure and to generate a second pressure signal, and at least two data lines, wherein the at least two data lines comprise a first blood pressure data line and a second blood pressure data line, and the method further comprises:

receiving, with the control unit, a first pressure signal from the first pressure sensor;

receiving, with the control unit, a second pressure signal from the second pressure sensor;

generating, with the blood pump, pressure pulses in the extracorporeal blood circuit upstream of the dialyzer;

transmitting and attenuating the pressure pulses via the semipermeable membrane;

splitting up the second pressure signal measured downstream of the dialyzer into a fundamental component and at least one harmonic;

determining the longitudinal flow resistance based on a ratio of the fundamental component and the at least one harmonic; and determining, with the sensor system and the control unit, the transmembrane pressure via a blood pressure signal, the first pressure signal, and a second pressure signal.

* * * * *